United States Patent [19]
Oliver et al.

[11] Patent Number: 5,282,563
[45] Date of Patent: Feb. 1, 1994

[54] FLOSS DISPENSERS

[75] Inventors: Darcy D. Oliver, Veradale; Ross D. Thurber, Spokane; Terrance R. Folsom, Greenacres, all of Wash.

[73] Assignee: De Voe G. Quinton, Spokane, Wash.

[21] Appl. No.: 956,000

[22] Filed: Oct. 1, 1992

[51] Int. Cl.⁵ .................... B65H 75/32; A61C 15/04
[52] U.S. Cl. .......................... 225/47; 225/46; 225/51; 225/53; 225/77; 225/90
[58] Field of Search .............. 225/6, 47, 46, 51, 53, 225/77, 80, 90; 242/137, 137.1, 138; 132/323, 324, 325

[56] References Cited

U.S. PATENT DOCUMENTS

| | | |
|---|---|---|
| 199,040 | 1/1878 | Doak . |
| 745,833 | 12/1903 | Hanson . |
| 750,574 | 1/1904 | Bicket . |
| 810,292 | 1/1906 | Meaker . |
| 897,822 | 9/1908 | Dougherty . |
| 1,287,926 | 12/1918 | Ecaubert . |
| 2,371,686 | 3/1945 | Gaulke . |
| 2,479,710 | 8/1949 | Arnold . |
| 2,488,492 | 11/1949 | Dumbleton . |
| 2,681,772 | 6/1954 | Charney . |
| 2,707,782 | 5/1955 | Eby ........................ 132/324 |
| 2,942,764 | 6/1960 | Castelli ..................... 225/51 |
| 3,071,299 | 1/1963 | Brown . |
| 3,136,462 | 6/1964 | Knutson . |
| 3,246,815 | 4/1966 | Aronson ..................... 225/44 |
| 3,265,264 | 8/1966 | Stephens . |
| 4,026,063 | 5/1977 | Allen et al. ............... 43/54.5 R |
| 4,634,077 | 1/1987 | Wilson ..................... 242/139 |
| 4,925,073 | 5/1990 | Tarrson et al. .............. 225/44 |
| 5,054,674 | 10/1991 | Fortman .................... 225/6 |
| 5,160,077 | 11/1992 | Sticklin .................... 225/38 |

Primary Examiner—Hien H. Phan
Attorney, Agent, or Firm—Wells, St. John, Roberts, Gregory & Matkin

[57] ABSTRACT

A floss dispenser according to one embodiment has a base with a spool housing provided on one end thereof and a cutting member provided on the other end. The spool housing holds a spool of dental floss and dispenses an exposed portion of floss through an output port above the base. The cutting member has a friction element (which includes a blade for cutting the floss) positioned on an upper end thereof across from the output port. The friction element holds a distal end of the exposed portion of floss a spaced distance from the output port so that the exposed portion of floss extends above the base and through a gap region between the output port and the cutting member. The gap region is sized such that a user can grasp the exposed portion of floss without contacting any part of the floss dispenser. In this manner, the user avoids contaminating the floss dispenser.

20 Claims, 10 Drawing Sheets

FLOSS DISPENSERS

TECHNICAL FIELD

This invention relates to dental floss dispensers.

BACKGROUND OF THE INVENTION

Dental floss is commonly housed within a hand-sized plastic container. The dental floss is wound about a cardboard or plastic core which is rotationally mounted within the plastic container so that the floss can be unwound from the core. The container has an opening through which an exposed portion of the floss is dispensed. The dental floss container also has a small blade or cutter positioned near the opening which is used to sever a segment of floss.

These conventional floss dispensers have an inherent drawback in that they are susceptible to contamination. To withdraw floss from one such dispenser, a user grasps the container with one hand and the exposed portion of the floss with the other hand. The user pulls the floss to unwind it to a desired length and then severs it. Unfortunately, the exposed portion of floss extending from the container opening to the cutter lies very close to, and often in contact with, the plastic container causing the user to touch the container when handling the exposed portion of floss. That is, a user cannot pinch the exposed portion of the floss with his or her fingers without contacting the plastic container. As a result, the floss container is contaminated by both the support hand which grasps the container and the other hand which touches the container when handling the exposed portion of the floss.

The issue of contamination is particularly important in the dental office environment. Dentists and dental hygienists work with several patients every day. While these professionals typically wear a new pair of sterilized gloves for each patient, the same floss dispenser is often used throughout the day. A problem arises in that the professional might contaminate the floss dispenser with germs or diseases of one of his or her patients and effectively transfer theses germs to another patient.

Another available alternative is to use a new floss dispenser with each patient. However, this practice is expensive.

The necessity of maintaining sterile environments in a dental office setting is becoming increasingly important with the onslaught of infectious diseases, such as AIDS. It is desirable to construct a floss dispenser which does not require the dentists or dental hygienist to handle it and thus, could be used for many different patients.

A second inherent drawback in conventional floss dispensers is that they are cumbersome to handle because one must use two hands to cut a desired strip of floss. This is often inconvenient for a dentist or dental hygienist because they must stop what they are presently doing and use both hands to pick up the floss container and cut a piece of floss.

This invention provides many types of floss dispensers which conveniently rest on, or mount to, a surface and which dispense floss in such a manner that the user does not contact the dispenser and thus, does not contaminate it.

BRIEF DESCRIPTION OF THE DRAWINGS

The preferred embodiments of the invention are described below with reference to the following accompanying drawings.

FIG. 1 is side elevation view of a floss dispenser according to a first embodiment of this invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

FIGS. 1-4 illustrate a first embodiment of a floss dispenser 20 constructed according to this invention. Floss dispenser 20 is designed to rest on top of a surface 21 (FIG. 1), such as a table, desk, or dental tray. Floss dispenser 20 has a base 22 with a first or rear end 24 and a second or front end 26. Floss dispenser 20 has a cylindrically shaped spool housing 28 provided at first end 24 of base 22 which defines a chamber 33 (FIG. 3) for holding a spool of dental floss 29 along a substantially vertical axis 30. More specifically, spool housing 28 has an internal cylindrical surface 34 provided about, and radially spaced from, a central rod 32 (which is aligned along axis 30) to define chamber 33. Spool 29 slides over rod 32, and is free to rotate about it within chamber 33 as the dental floss is unwound and dispensed from spool housing 28.

A removable lid 36 is provided on top of spool housing 28 to enclose the spool of dental floss within the chamber. Lid 36 has a lower annular sleeve 38 sized to fit within and loosely abut interior surface 34. Lower sleeve 38 has an inverted U-shaped opening 40 formed therein to assist in guiding the floss from the spool housing. Lid 36 further includes a lip 42 formed adjacent to sleeve 38 and sized to rest on top of an annular rim 35 (FIG. 2) of spool housing 28.

Floss dispenser 20 has an output port 44 (FIGS. 1 and 3) defined between lid 36 and spool housing 28 through which an exposed portion of floss 46 is dispensed. Output port 44 is at a first elevation or height $H_1$ above base 22. Lip 42 of lid 36 and upper rim 35 of spool housing 28 form a nip for floss 46 to impart a small friction thereon.

Figure 2:
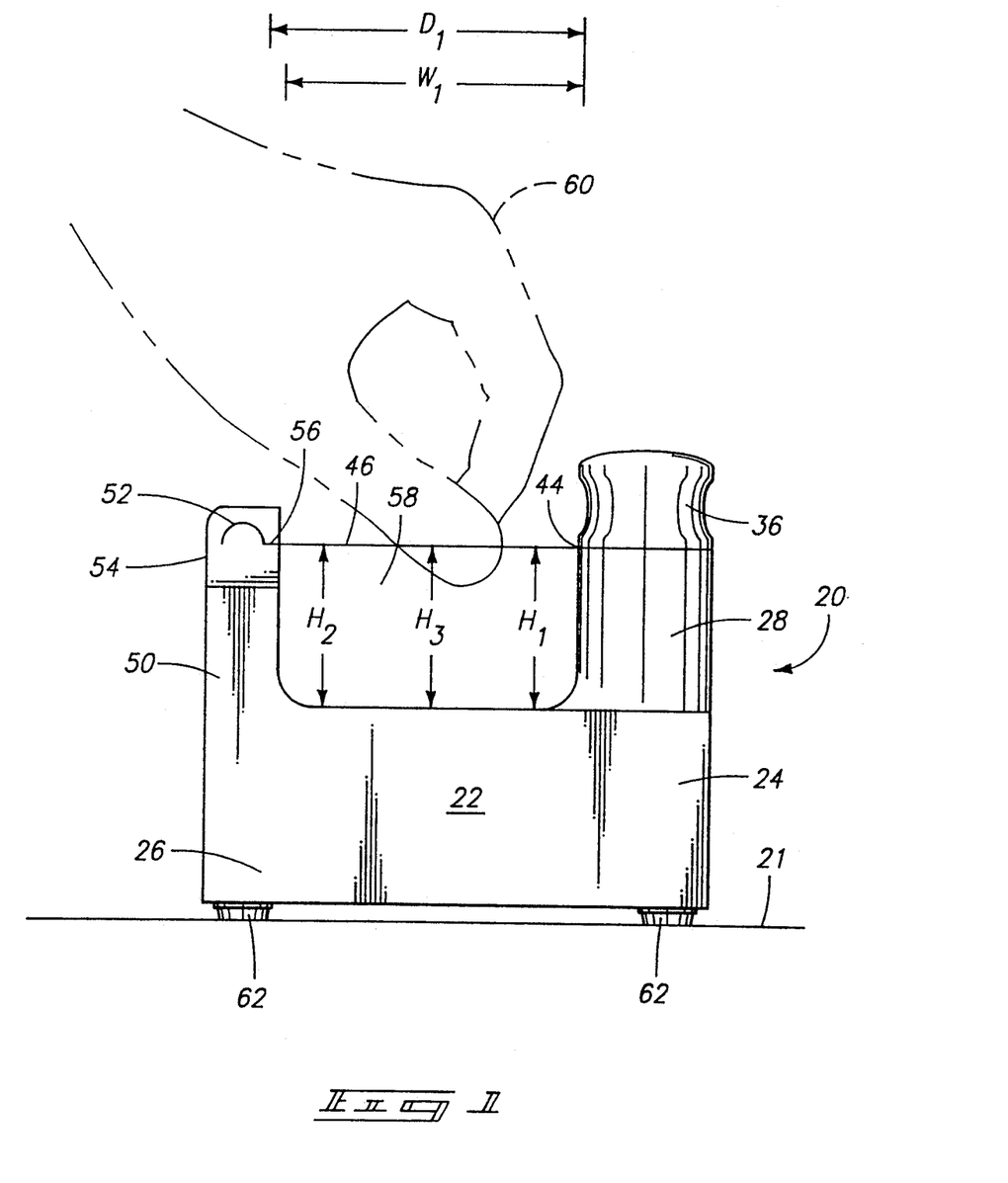
FIG. 2 is a perspective view of the FIG. 1 floss dispenser.
Figure 3:
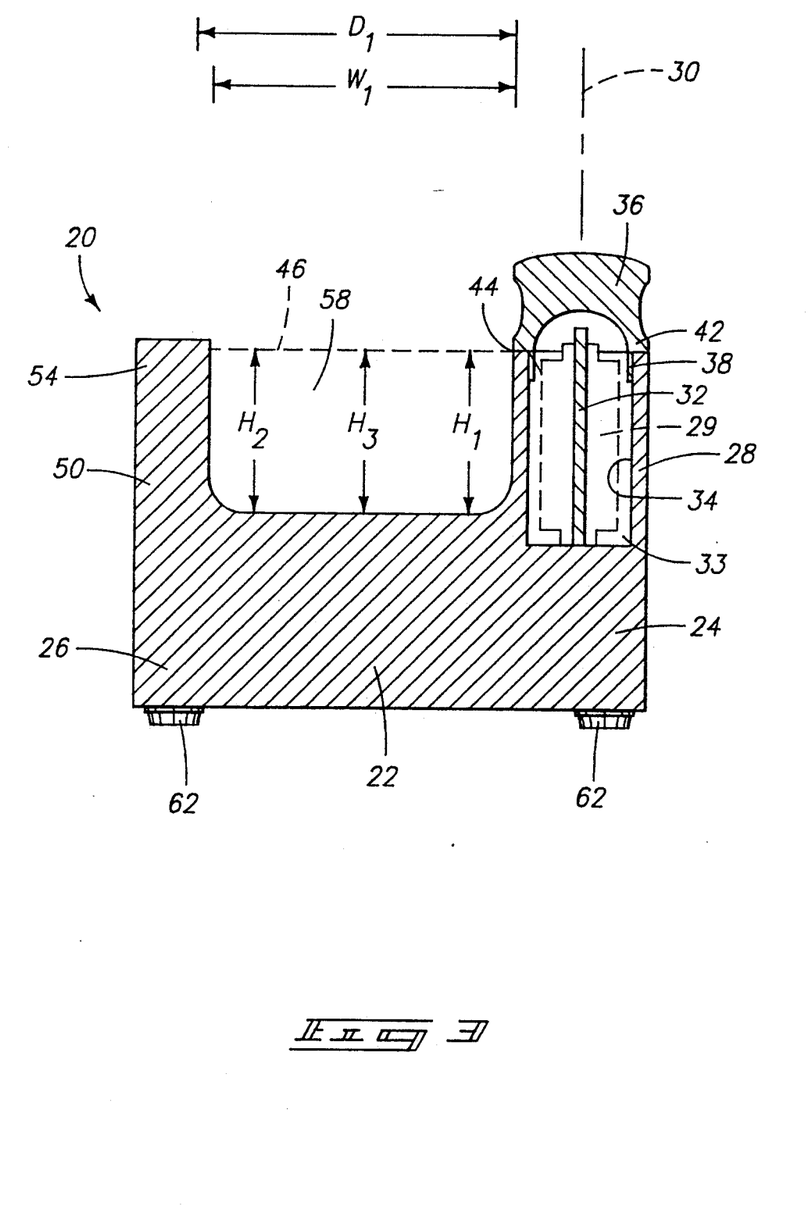
FIG. 3 is a cross-sectional view taken through lines 3—3 in FIG. 2.
Figure 4:
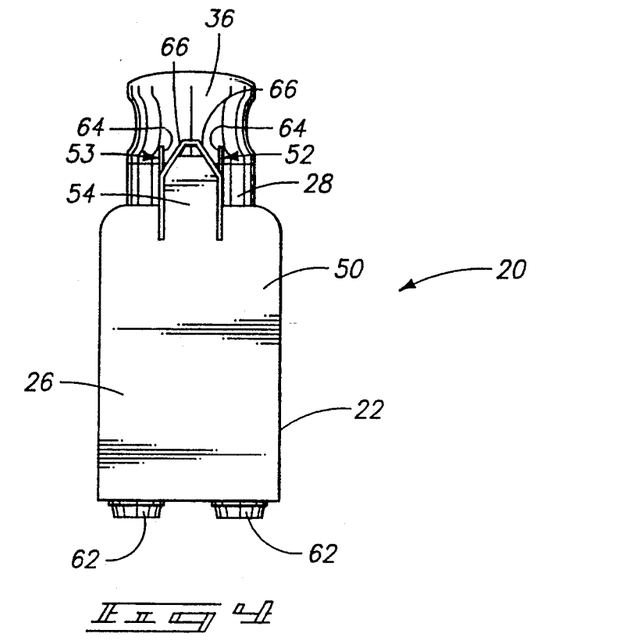
FIG. 4. is an end view of the FIG. 1 floss dispenser.

Dental floss container 20 has a cutting member 50 which extends upward from second end 26 of base 22. Cutting member 50 has friction elements 52 and 53 positioned on opposing sides of upper end 54 (FIG. 4). Friction element 52 (or 53) holds a distal end 56 (FIG. 1) of the exposed portion of floss 46 at a spaced distance $D_1$ from output port 44. Friction element 52 is positioned at a second elevation or height $H_2$ relative to base 22. Floss 46 thereby extends between spool housing 28 and friction element 52 elevationally above base 22 at a height which varies between the elevation of output port 44 (at height $H_1$) and the elevation of friction element 52 (at height $H_2$). Floss 46 is at a height $H_3$ at its center. Preferably, first height $H_1$ of output port 44 is approximately equal to the second height $H_2$ of friction element 52 relative to base 22. In this manner, the exposed portion of floss 46 extends substantially horizontally between output port 44 and friction element 52 (i.e., heights $H_1$, $H_2$, and $H_3$ are all approximately equal).

Floss 46 extends through a gap region 58 which is defined as the void area above base 22 and between spool housing 28 and cutting member 50. Gap region 58 has a width $W_1$ and a medial height $H_3$.

Height $H_3$ of the exposed portion of floss 46 relative to base 22 and width $W_1$ of gap region 58 are sufficient to permit a user to grasp the exposed portion of floss 46 without contacting floss dispenser 20. More specifically, height $H_3$ is sufficient to allow at least one finger 60 (FIG. 1) of the user to be inserted between floss 46 and base 22 without contacting base 22. Preferably, the user can place two or three fingers through gap 58 without contacting any portion of floss dispenser 20. In the preferred embodiment shown in FIGS. 1-4, height $H_3$ is at least approximately one-half of width $W_1$ of gap region 58. However, the medial height can be varied by designing output port 44 and friction element 52 closer to, or farther from, base 22. Accordingly, in another embodiment (such as the embodiment shown in FIGS. 5-7), the medial height can be greater than width $W_1$ of gap region 58.

As shown in FIG. 4, each friction element 52 and 53 constitutes a V-shaped groove between a first projecting member or wall 64 and a second projecting member or wall 66. First wall 64 has a crescent shaped peripheral edge (FIGS. 1 and 2) which is sharpened to form a cutting edge or blade used to sever the floss. Friction elements 52 and 53 thereby provide a dual purpose of (1) cutting a segment of dental floss extending beyond the friction element by pulling the dental floss across the blade or cutter defined by crescent shaped wall 64, and (2) holding a distal end of the dental floss after the segment has been cut.

Floss dispenser 20 has four rubber or elastomer feet 62 positioned at the four corners of base 22. Feet 62 provide traction to facilitate a non-slide mount on surface 21. Alternatively, floss dispenser 20 could be adapted with a single rubber or elastomer sheet covering the entire bottom surface of base 22.

Base 22, spool housing 28, and cutting member 50 are preferably formed of aluminum as a single unit. Such can be machined or formed in a cast to attain the desired shape. Rod 32 and lid 36 are formed separately and later assembled. Friction elements 52 and 53 are formed of a malleable metal which is bent into the illustrated shape and mounted to cutting member 50. The crescent shaped walls 64 are cut out from the piece of metal to form the V-shaped groove. The floss dispenser has sufficient weight and traction to resist movement along the surface while a user pulls a piece of floss from the spool housing. It is also portable.

The floss dispenser of this invention is advantageous over prior art dispensers in that a dentist or dental hygienist can quickly and efficiently grasp and cut a segment of floss without contacting and contaminating the floss dispenser. Additionally, the dental professional can cut a segment of floss using only one hand which frees the other hand to attend to his or her patient.

Figure 5:
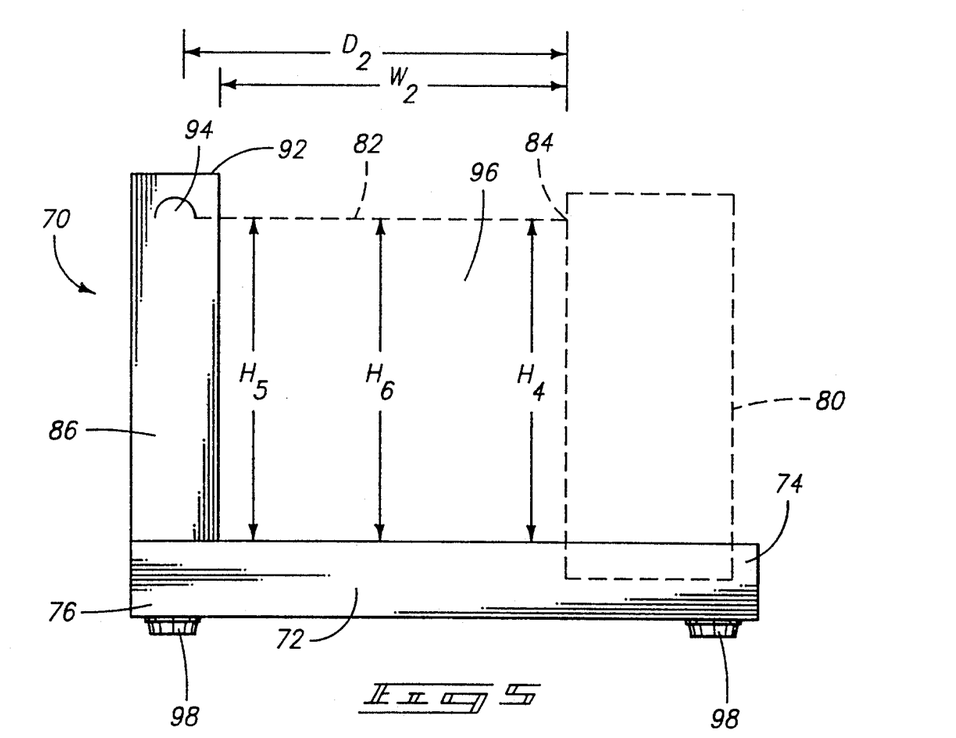
FIG. 5 is a side elevation view of a floss dispenser according to a second embodiment of this invention.
Figure 6:
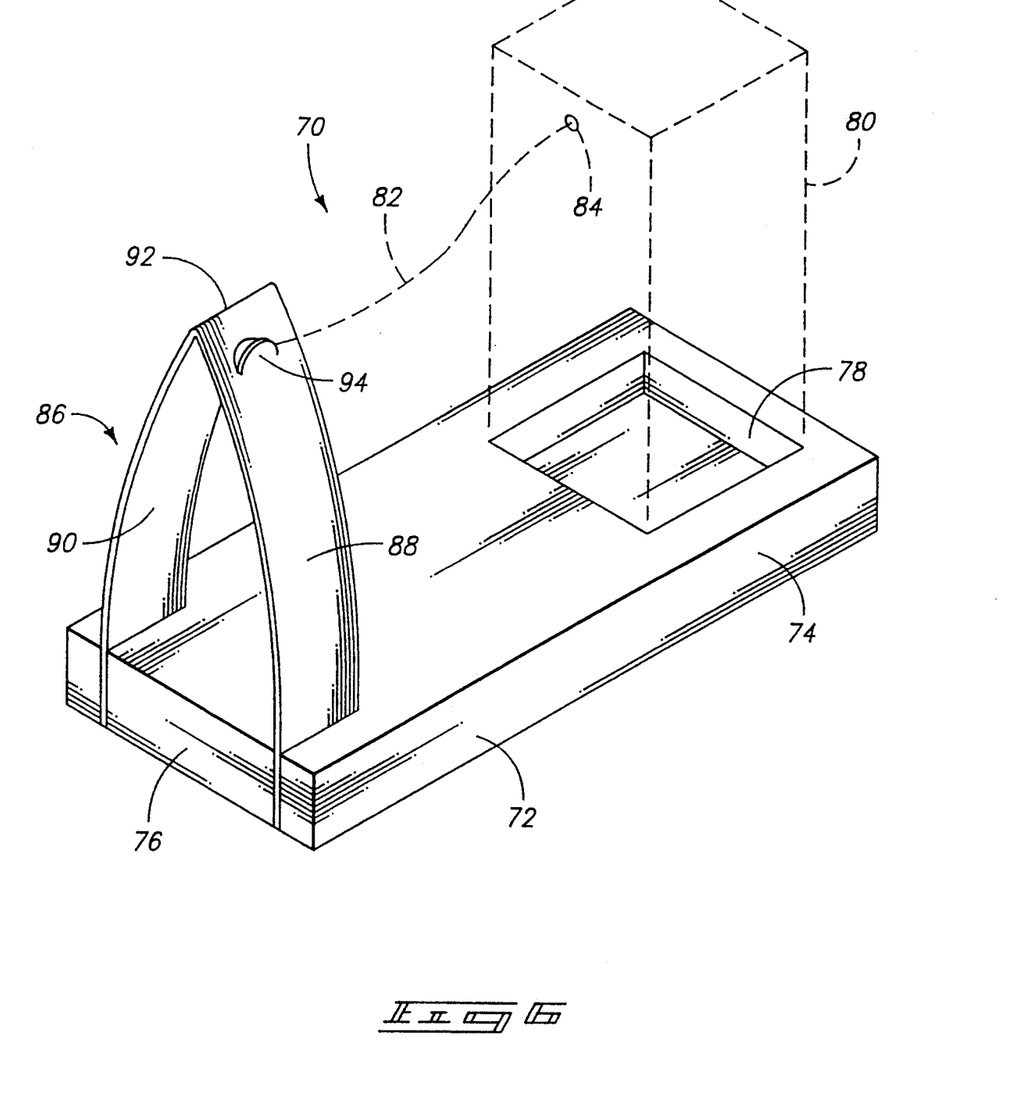
FIG. 6 is a perspective view of the FIG. 5 floss dispenser.
Figure 7:
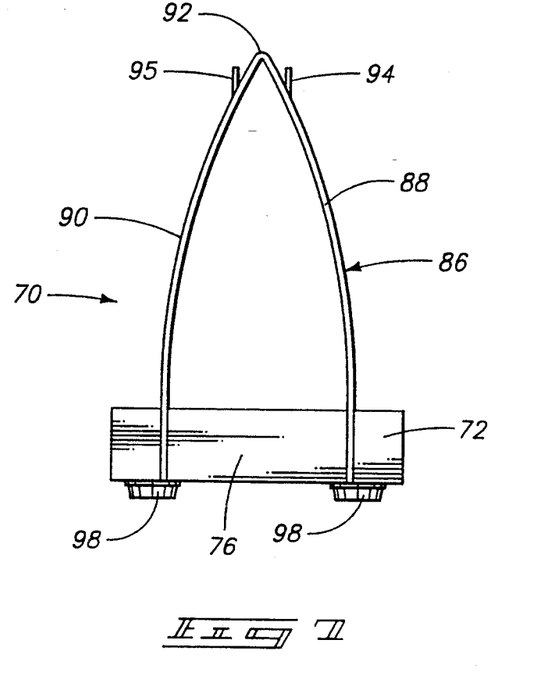
FIG. 7 is an end view of the FIG. 5 floss dispenser.

FIGS. 5-7 show a second embodiment of a floss dispenser 70 according to this invention. Floss dispenser 70 includes a base 72 having a first or rear end 74 and a second or front end 76. Base 72 has a rectangular recessed region 78 (FIG. 6) provided in the top surface at the first end 74 of base 72. Recessed area 78 is sized and shaped to receive a dental floss container 80 (shown in phantom). Container 80 houses a spool of dental floss, and dispenses an exposed portion of floss 82 through an opening 84 provided in the container. Such dental floss containers are commercially available, and come in different shapes. Recess 78 is shaped to be complementary to the shape of the commercially available container. For dental floss container 80 which has a rectangular base, recess 78 is rectangular shaped so that the base of dental floss container 80 fits snugly therein. For a circular container shape, however, recess mount 78 would be circular to provide compatible mount.

Floss dispenser 70 has a cutting member 86 which extends upward from second end 76 of base 72 to an upper end or apex 92. Cutting member 86 has two legs 88 and 90 which arranged in an inverted V-shape and extend upward from base 72 to an apex 92. Cutting member 86 also includes two friction elements 94 and 95 (FIG. 7) which are provided on respective legs 88 and 90 adjacent to apex 92. Friction elements 94 and 95 are similar in shape and construction to friction elements 52 and 53 described above with reference to FIG. 4. That is, each friction element has a groove defined in part by a crescent-shaped wall, the edge of which is sharpened to form a blade for cutting the exposed portion of floss. Floss dispenser 70 also has four rubber feet 98 positioned at the four corners of base 72.

When container 80 is properly inserted into recess 78, opening 84 is positioned at an elevational height $H_4$ above base 72. Friction elements 94 and 95 are positioned at an elevation $H_5$ above base 72 and hold a distal end of the exposed portion of floss 82 a spaced distance $D_2$ from dental floss container 90 held in the recess mount 78. Dental floss 82 is suspended at an elevation relative to base 72 which varies from height $H_4$ and $H_5$ through a central height $H_6$. Preferably, the elevations of container opening 84 and friction elements 94 and 95 (i.e., heights $H_4$ and $H_5$) are approximately equal so that the exposed portion of floss 82 extends substantially horizontally between container opening 84 and friction elements 94 and 95 (i.e., heights $H_4 \approx H_5 \approx H_6$).

The exposed portion of floss 82 extends through a gap region 96 (FIG. 5) which is defined as the void area above base 72 and between container 80 (when mounted) and cutting member 86. Gap region 86 has a medial height $H_6$ and a width $W_2$ which are sufficient to permit a user to grasp the exposed portion of floss 82 without contacting any portion of the floss dispenser. Height $H_6$ is sufficient to allow a user to insert at least one finger (and preferably, two to three fingers) between the exposed portion of floss 82 and the base 72 without contacting base 72. Height $H_6$ is preferably greater than width $W_2$ of gap region 96. However, in an alternative embodiment, the medial height might be less than width $W_2$ (for example, the medial height might be approximately one-half of width $W_2$).

This again is advantageous in that the dentist or dental hygienist can easily handle and cut a piece of floss without contaminating any portion of the floss dispenser or dental floss container. Additionally, the dental professional can operate the floss container with one hand, thereby freeing the other hand to continue working with the patient.

Base 72 of floss dispenser 70 is preferably formed of aluminum. Cutting member 86 is preferably formed of a malleable metal which can be bent into the V-shape. It is then inserted into preformed grooves provided in base 72 to fixedly mount cutting member 86 to base 72. Floss dispenser 70 has sufficient weight and traction to allow a user to pull dental floss from container 80 without displacing dispenser 70.

Figure 8:
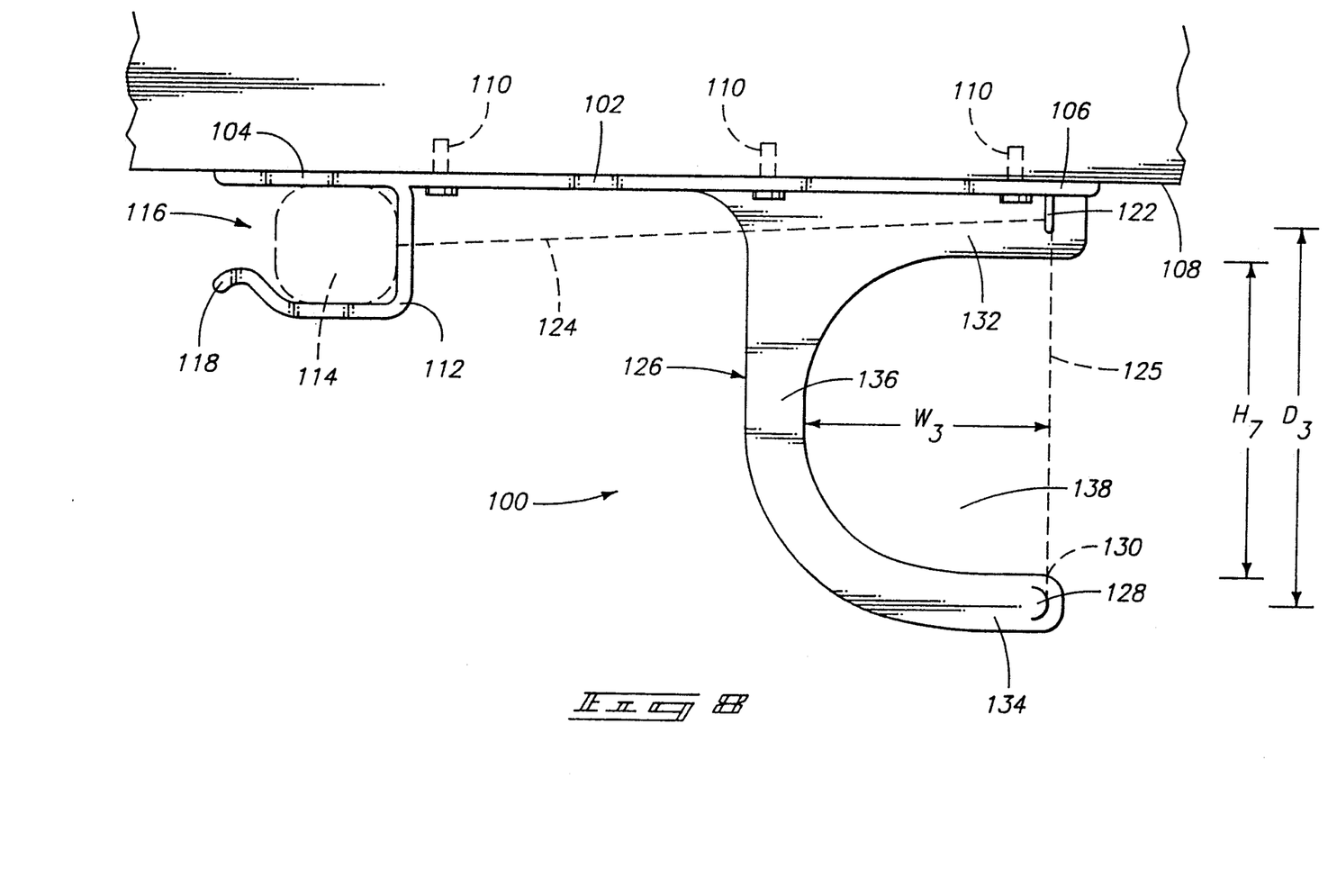
FIG. 8 is a side elevation view of a floss dispenser according to a third embodiment of this invention.
Figure 9:
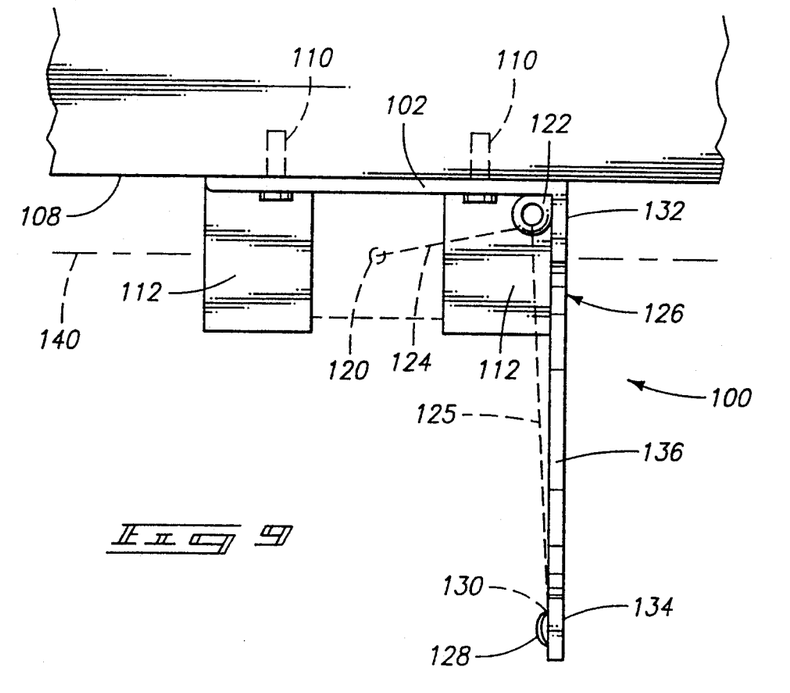
FIG. 9 is an end view of the FIG. 8 floss dispenser.

FIGS. 8-9 illustrate a third embodiment of a floss dispenser 100 constructed according to this invention. Floss dispenser 100 has a base 102 with a first or back end 104 and a second or front end 106. Base 102 consists of a flat, thin plate which is mountable via screws 110 to a surface 108, such as the underside surface of a table. Floss dispenser 100 includes two clamps 112 provided on first end 104 of base 102 which hold a dental floss container 114. Each clamp 112 has a deflectable end portion 118 (FIG. 8) which yields to provide a variable-sized opening 116 as dental floss container 114 is inserted into, or removed from, the clamps. In this manner, clamps 112 provide a cradle means for releasible retaining disposable dental floss container 114.

The dental floss container shown in FIGS. 8 and 9 is commercially available and consists of a plastic housing which holds a spool of dental floss and dispenses an exposed portion of dental floss 124 through a central opening 120 (FIG. 9). Dental floss container typically has a blade or cutting unit provided thereon, but such goes unused when the container is employed in conjunction with floss dispenser 100.

Floss dispenser 100 has an intermediate guide element 122 which is spaced from clamps 112 to direct an exposed portion of floss 124 along an intermediate path. Guide element 122 is an annular or circular shaped member through which the exposed portion of floss passes. Intermediate guide element 122 has a smooth inner surface to prevent snagging the floss. Guide element 122 can have other shapes, such as square, octagonal, etc. Further, the guide element need not be entirely enclosed, but can be, for example, U-shaped with an opening at the top wherein the floss rides at the bottom portion of the U-shaped element.

Floss dispenser 100 has a cutting member 126 which extends downwardly from the second or front end 106 of base 102. Cutting member 100 is C-shaped with a first or upper end 132 adjacent to base 102, a second or lower end 134, and a middle section 136. Intermediate guide element 122 is positioned adjacent to first end 132 and is fixedly mounted to cutting member 126, or base 102, or both. Cutting member 126 has a friction element 128 positioned at second end 134 which holds a distal end 130 of the exposed portion of floss 125 a spaced distance $D_3$ from intermediate guide element 122. The exposed portion of floss 125 extending between intermediate element 122 and friction element 128 is offset a selected distance from middle section 136.

A gap region 138 is defined as the void area bound by the C-shaped cutting member. Gap region 138 has a height $H_7$ between upper and lower ends 132, 134 of C-shaped member 126 and a width $W_3$ at middle section 136. Height $H_7$ and width $W_3$ of gap region 138 is sized to permit a user to grasp the exposed portion of floss 125 without contacting any portion of floss dispenser 100. More specifically, width $W_3$ is sufficient to allow a user to insert at least one finger (and preferably, two to three fingers) between the exposed portion of floss 125 and middle section 136 without contacting middle section 136 or the upper or lower ends 132, 134 of C-shaped cutting member 126. Preferably, width $W_3$ is at least approximately one-half of the height $H_7$ of gap region 138. However, in other embodiments, the C-shaped member 126 may be sized such that the medial width is greater than height $H_7$.

Dental floss container 114 is retained along a first axis 140 (FIG. 9), while the intermediate guide element 122 directs the exposed portion of floss 124 along an intermediate path which is substantially perpendicular to axis 140. The exposed portion of floss 125 then extends between intermediate guide element 122 and friction element 128 along a path which is substantially perpendicular to the intermediate path. While this is preferred, floss dispenser 100 may be designed such that cutting member 126 lies in the same plane as base 102 to extend beyond an edge of a table or counter such that the exposed portion of floss 125 between intermediate guide element 122 and friction element 128 lies along a path which is substantially parallel to axis 140.

Friction element 128 is similar to friction elements 52, 53 and 94, 95 which are described above. Particularly, friction element 128 is capable of both holding the distal end 130 of the exposed portion of floss and cutting any segment of floss beyond the friction element.

Floss dispenser 100 is formed of a malleable metal or a molded plastic. When it is formed of metal, the floss dispenser can be manufactured from a single sheet which is cut and then bent into the illustrated shape. That is, C-shaped clamps 112 and the C-shaped cutting member 126 are folded to extend laterally from the plane containing base 102.

Figure 10:
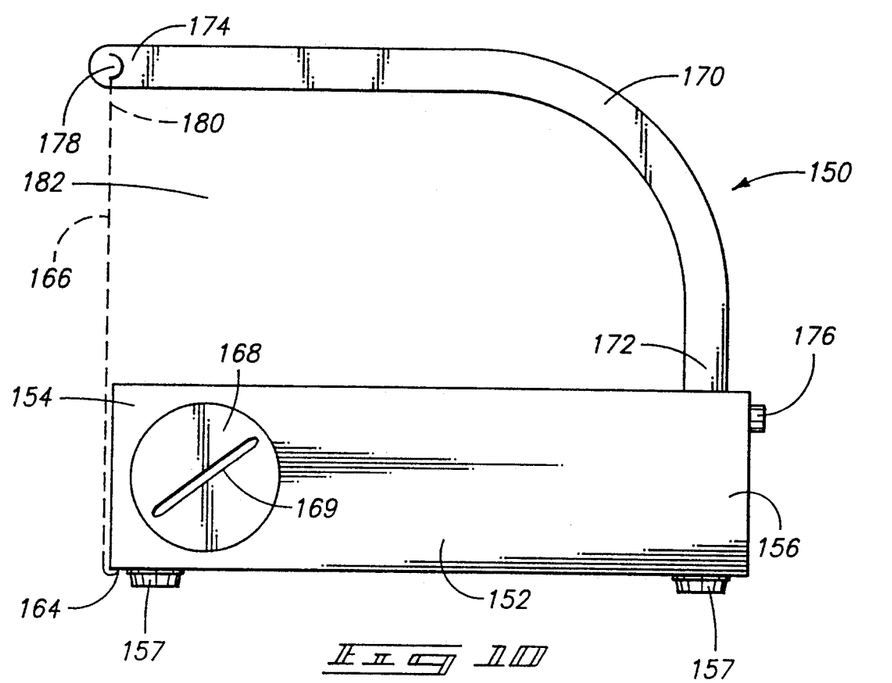
FIG. 10 is a side elevation view of a floss dispenser according to a fourth embodiment of this invention.
Figure 11:
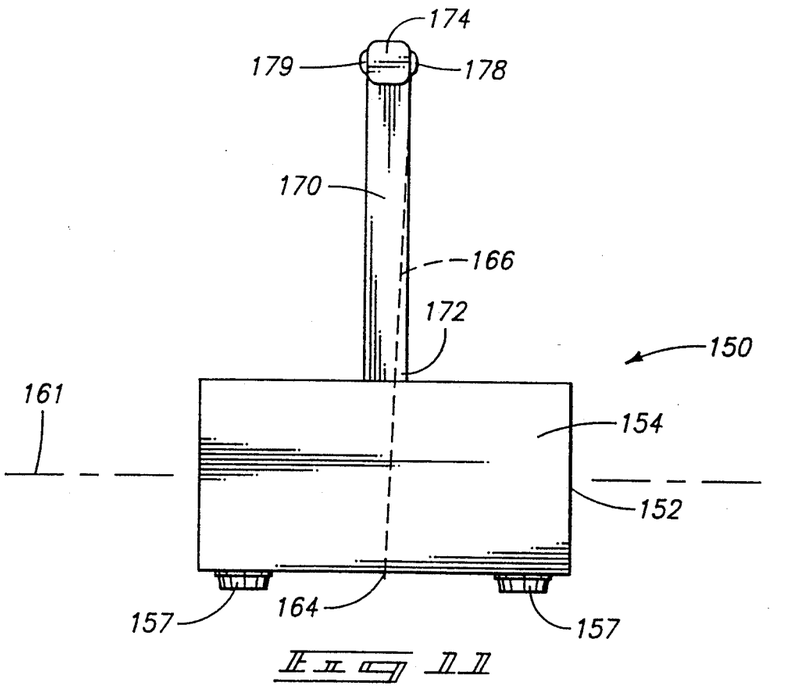
FIG. 11 is an end view of the FIG. 10 floss dispenser.
Figure 12:
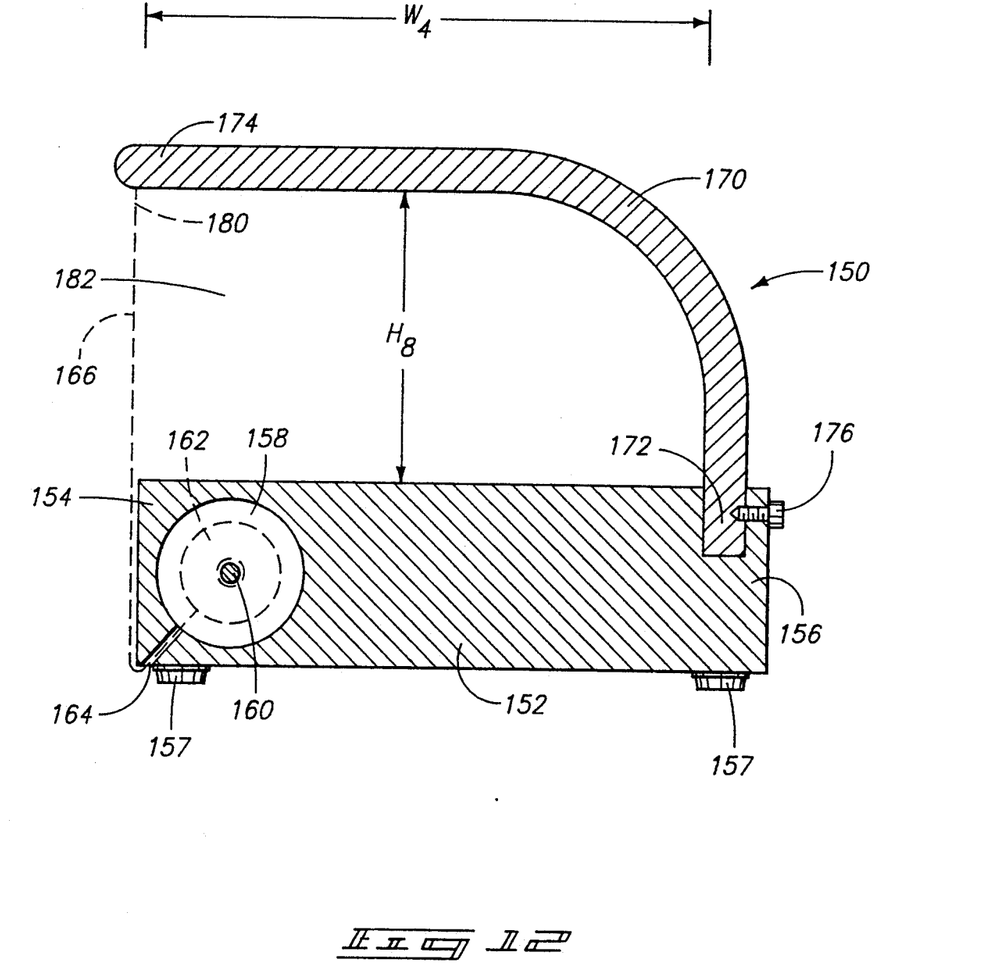
FIG. 12 is a cross-sectional diagram taken centrally through the FIG. 10 floss dispenser.

FIGS. 10-12 illustrate a fourth embodiment of a floss dispenser 150 constructed according to this invention. Floss dispenser 150 has a base 152 with a first or front end 154 and a second or rear end 156 and four rubber feet 157 provided on the four corners of base 152. A spool chamber 158 (FIG. 12) is formed in first end 154 of base 152 and holds a spool of dental floss 162 about a central horizontal rod 160 along a horizontal axis 161 (FIG. 11). The spool of dental floss 162 has an inner core (typically formed of cardboard or plastic) which slides over rod 160 as shown in FIG. 12 and is free to rotate about rod 160 as floss is unwound from spool 162.

Base 152 has an output port 164 which provides access from spool chamber 158 to the exterior of base 152. An exposed portion of floss 166 is dispensed through output port 164. While output port is shown as being angled to the bottom corner of base 152, it can extend horizontally to provide an opening midway up end 154 of base 152 (as shown, for example, in FIG. 13). A removable lid 168 (FIG. 10) is provided on the side of base 152 to facilitate replacement of the spool of dental floss 162. The lid is preferably threaded and can be screwed tight to be flush with base 152. A slot 169 is formed in lid 168 to receive a screwdriver or other instrument.

Floss dispenser 150 also has a cutting member 170 which has a lower end 172 mounted to base 152 and an upper end 174 which extends over and elevationally above first base end 154. Lower end 172 of cutting member 170 fits within a preformed recess in base 152 and is secured therein by a screw 176. Other mounting arrangements are possible. Additionally, the cutting member and base can be formed as in integral unit (such as shown in FIG. 13).

Cutting member 170 has two friction elements 178 and 179 (FIG. 11) mounted to opposing sides of upper end 174. Friction elements 178 and 179 are similar to the friction elements discussed above in that they have a dual purpose of holding and cutting the floss. The friction elements are positioned above output port 164 and hold a distal end 180 of the exposed portion of floss 166 a spaced distance from output port 164. In this manner, the exposed portion of floss extends upwardly in a direction substantially perpendicular to horizontal axis 161 and across a gap region 182 which is defined as the void area bound by cutting member 170 and base 152.

Gap region 182 has a selected height $H_8$ (FIG. 12) between base 152 and cutting member 170. Additionally, gap region 182 has a width $W_4$ defined by a longitudinal distance between the exposed portion of floss 166 and the relatively vertical portion of cutting member 170. This longitudinal distance or width $W_4$ relative to cutting member 170 and height $H_8$ of gap region 182 is sufficient to permit a user to grasp the exposed portion of floss 166 without contacting any part of floss dispenser 150. More specifically, gap region 182 is sized to allow a user to insert at least one finger (and preferably, two to three fingers) between the exposed portion of floss 166 and cutting member 170 without contacting the cutting member. Preferably, width $W_4$ is greater than height $H_8$, but in alternative embodiments, this medial width can be less than the height (for example, approximately one-half of height $H_8$).

Figure 13:
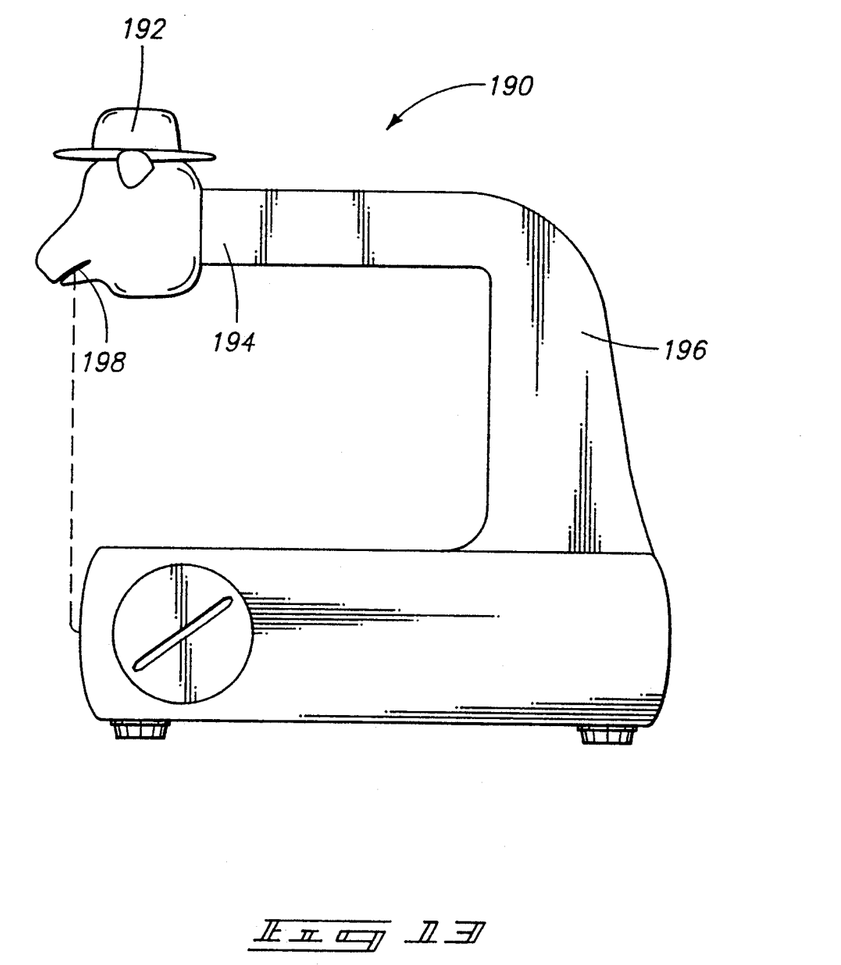
FIG. 13 is a side elevation view of a modified floss dispenser similar to the FIG. 10 floss dispenser.

FIG. 13 shows a floss dispenser 190 which is a modified version of floss dispenser 150 of FIGS. 10-12 which is more suitable and attractive for children to encourage daily flossing. A cartoon character or animal head 192 is mounted on upper end 194 of cutting member 196. This head is formed of plastic or metal with a friction element 198 (and cutting blade) conveniently positioned in it. For example, friction element 198 is mounted in the mouth of bear head 192, but could also be mounted in its ears or nose. This modified embodiment provides an attractive dispenser which can be left out on a bathroom shelf to encourage children to floss more regularly.

The four above embodiments are all advantageous over prior art floss dispensers. Each one holds a spool of floss in such an arrangement that an exposed portion of floss extends through a gap region which is dimensioned to allow a user to handle the exposed portion of floss without contacting any portion of the floss dispenser. In this manner, dentists or their assistants do not contaminate the floss dispensers. Additionally, each dispenser is designed to rest on top of a table or tray, or to be mounted to a surface (such as the underside of a table) so that a user can operate the dispenser with only one hand. The disclosed embodiments show several different techniques for holding a spool of dental floss. For example, in the first and fourth embodiments (FIGS. 1-4 and 10-12), the spool of dental floss rests in a chamber. In the second embodiment (FIGS. 5-7), a commercially available dental floss container is held in a recessed mount. In the third embodiment (FIGS. 8-9), a commercially available dental floss container is releasibly retained in C-shaped clamps. Each of these techniques constitute a spool mounting means for holding a spool of dental floss and facilitating dispensement of that floss.

In compliance with the statute, the invention has been described in language more or less specific as to structural or methodical features. It is to be understood, however, that the invention is not limited to the specific features described or shown, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A floss dispenser comprising:
 a base having first and second ends and an upper surface, the first base end having a recessed mount formed in the upper surface for receiving and holding a dental floss container having a spool of dental floss enclosed within a casing, the recessed mount in the upper surface of the base being sized to fittingly engage a lower end of the casing of the dental floss container when the dental floss container is inserted into the recessed mount to thereby support the dental floss container;
 the dental floss container dispensing an exposed portion of floss through an opening in an upper end of the casing of the dental floss container, the opening being at a first elevation above the base;
 a cutting member extending upward from the second base end and having an upper end, the cutting member including a friction element positioned at the upper end at a second elevation above the base, the friction element holding a distal end of the exposed portion of floss a spaced distance from the dental floss container held in the recessed mount so that the exposed portion of floss extends elevationally at a height above the base and across a gap region of a selected width between the dental floss container and the cutting member, the height of the exposed portion of floss relative to the base and the width of the gap region being sufficient to permit a user to grasp the exposed portion of floss extending between the dental floss container and the friction element without contacting the floss dispenser; and
 the cutting member further including a blade mounted on the upper end thereof for cutting an exposed portion of floss.

2. A floss dispenser according to claim 1 wherein:
 the height of the exposed portion of dental floss relative to the base is sufficient to allow a user to insert at least one finger between the exposed portion of dental floss and the base without contacting the base.

3. A floss dispenser according to claim 1 wherein:
 the height of the exposed portion of dental floss relative to the base is at least approximately one-half of the width of the gap region between the dental floss container and the cutting member.

4. A floss dispenser according to claim 1 wherein:
 the height of the exposed portion of dental floss relative to the base is greater than the width of the gap region between the dental floss container and the cutting member.

5. A floss dispenser according to claim 1 wherein:
 the first elevation of the opening of the dental floss container held in the recessed mount of the base relative to the base is approximately equal to the second element of the friction element relative to the base; and the exposed portion of floss extends substantially horizontally between the container opening and the friction element, the height of the exposed portion of floss relative to the base being at least approximately one-half of the width of the gap region.

6. A floss dispenser according to claim 1 wherein:
the friction element comprises a groove between first and second walls, the first wall having a crescent shaped peripheral edge, the peripheral edge defining the blade of the cutting member.

7. A floss dispenser according to claim 1 wherein:
the cutting member has two friction elements mounted on opposing sides of the upper end.

8. A floss dispenser comprising:
a base having first and second ends, the first base end having a recessed mount for holding a dental floss container along a substantially vertical axis, the dental floss container housing a spool of dental floss and dispensing an exposed portion of floss through an opening in the container which is at a first elevation above the base;
a cutting member having two legs arranged in an inverted V shape which extend upward from the second base end to an apex and at least one friction element provided on one of the legs adjacent to the apex at a second elevation above the base, the friction element holding a distal end of the exposed portion of floss a spaced distance from the dental floss container held in the recessed mount so that the exposed portion of floss extends elevationally at a height above the base and across a gap region of a selected width between the dental floss container and the cutting member, the height of the exposed portion of floss relative to the base and the width of the gap region being sufficient to permit a user to grasp the exposed portion of floss extending between the dental floss container and the friction element without contacting the floss dispenser; and
the cutting member further including a blade mounted on the upper end thereof for cutting an exposed portion of floss.

9. A floss dispenser comprising:
a base having first and second ends;
a spool housing provided at the first base end for holding a spool of dental floss and for dispensing an exposed portion of floss, the spool housing having an output port which is at a first elevation above the base and through which the exposed portion of floss is dispensed;
a cutting member extending upward from a lower end adjacent the second base end to an upper end, the cutting member having an inner surface facing the spool housing, an outer surface facing away from the spool housing, an upper surface transverse to the inner and outer surfaces and facing away from the base, and opposing side surfaces transverse to the inner, outer and upper surfaces;
the cutting member including a friction element positioned on at least one of the opposing side surfaces at the upper end at a second elevation above the base, the friction element holding a distal end of the exposed portion of floss a spaced distance from the output port so that the exposed portion of floss extends elevationally at a height above the base and through a gap region of a selected width between the spool housing and the cutting member, the height of the exposed portion of floss relative to the base and the width of the gap region being sufficient to permit a user to grasp the exposed portion of floss extending between the output port and the friction element without contacting the floss dispenser; and the friction element having a groove adjacent a projecting wall within which the distal end of the exposed portion of floss is held, the projecting wall having a peripheral edge which defines a blade for severing the exposed portion of floss, the friction element being arranged on the at least one of the opposing side surfaces of the cutting member such that the groove is aligned approximately in parallel with the exposed portion of floss when the floss extends between the spool housing and the cutting member and such that the distal end of the exposed portion of floss that is held within the groove is substantially aligned with the exposed portion of floss extending between the spool housing and the cutting member.

10. A floss dispenser according to claim 9 wherein the upper end of the cutting member is narrower than the lower end.

11. A floss dispenser according to claim 9 wherein:
the upper end of the cutting member is narrower than the lower end; and
the side surfaces have sections thereof which taper from the wider lower end to the narrower upper end.

12. A floss dispenser according to claim 9 further comprising multiple feet connected to the base.

13. A floss dispenser according to claim 9 wherein:
the height of the exposed portion of floss relative to the base is sufficient to allow a user to insert at least one finger between the exposed portion of floss and the base without contacting the base.

14. A floss dispenser according to claim 9 wherein:
the height of the exposed portion of floss relative to the base is at least approximately one-half of the width of the gap region between the spool housing and the cutting member.

15. A floss dispenser according to claim 9 wherein:
the height of the exposed portion of floss relative to the base is greater than the width of the gap region between the spool housing and the cutting member.

16. A floss dispenser according to claim 9 wherein:
the first elevation of the output port relative to the base is approximately equal to the second elevation of the friction element relative to the base; and
the exposed portion of floss extends substantially horizontally between the output port and the friction element, the height of the exposed portion of floss relative to the base being at least approximately one-half of the width of the gap region.

17. A floss dispenser according to claim 9, further comprising:
a removable lid for the spool housing, the output port being defined between the lid and the spool housing.

18. A floss dispenser comprising:
a base having first and second ends;
a spool housing provided at the first base end, the spool housing including a central rod aligned along a substantially vertical axis for holding a spool of dental floss, the housing having an internal surface about, and radially spaced from, the central rod to define a chamber;

a removable lid mountable to the spool housing for enclosing the chamber, the lid and the spool housing defining an output port which is at a first elevation above the base and through which an exposed portion of floss is dispensed;

a cutting member extending upward from its lower end adjacent the second base end to an upper end, the upper end being narrower than the lower end, the cutting member having an inner surface facing the spool housing, an outer surface facing away from the spool housing, an upper surface transverse to the inner and outer surfaces and facing away from the base, and opposing side surfaces transverse to the inner, outer and upper surfaces;

a friction element positioned on at least one of the opposing side surfaces at the upper end of the cutting member at a second elevation above the base, the friction element holding a distal end of the exposed portion of floss a spaced distance from the output port so that the exposed portion of floss extends elevationally at a height above the base and through a gap region of a selected width between the spool housing and the cutting member, the height of the exposed portion of floss relative to the base and the width of the gap region being sufficient to permit a user to grasp the exposed portion of floss extending between the output port and the friction element without contacting the floss dispenser; and the friction element having a groove adjacent a projecting wall within which the distal end of the exposed portion of floss is held, the projecting wall having a peripheral edge which defines a blade for severing the exposed portion of floss, the friction element being arranged on the at least one of the opposing side surfaces of the cutting member such that the groove is aligned approximately in parallel with the exposed portion of floss when it extends between the spool housing and the cutting member and such that the distal end of the exposed portion of floss that is held within the groove is substantially aligned with the exposed portion of floss extending between the spool housing and the cutting member.

19. A floss dispenser according to claim 18 wherein the side surfaces are tapered.

20. A floss dispenser according to claim 18 further comprising multiple feet connected to the base.

* * * * *